United States Patent
Domnisoru et al.

(10) Patent No.: US 6,598,013 B1
(45) Date of Patent: Jul. 22, 2003

(54) METHOD FOR REDUCING CROSS-TALK WITHIN DNA DATA

(75) Inventors: Cristian Domnisoru, Orono, ME (US); Mohamad Musavi, Orono, ME (US)

(73) Assignee: University of Maine, Bangor, ME (US)

( * ) Notice: Subject to any disclaimer, the term of this patent is extended or adjusted under 35 U.S.C. 154(b) by 0 days.

(21) Appl. No.: 09/918,885

(22) Filed: Jul. 31, 2001

(51) Int. Cl.$^7$ .............................................. G01N 27/26
(52) U.S. Cl. .......................... 702/191; 702/19; 702/20; 702/190; 204/456
(58) Field of Search ............................. 702/191, 19, 20, 702/22, 23, 25, 27, 28, 30–32, 66, 70, 71, 73–77, 106, 124, 126, 127, 183, 189, 190, 193, 195–197, 179, FOR 170, FOR 171, FOR 103, FOR 104, FOR 105, FOR 108, FOR 110, FOR 115–FOR 119, FOR 121, FOR 131, FOR 134, FOR 164, FOR 166, FOR 168; 706/924; 204/430, 451, 456, 457, 406, 407, 461, 606, 612; 382/129; 435/6, 91.1, 91.2, 287.1; 536/24.3; 436/172, 63; 422/82.07, 82.08, 68.1, 62; 356/344

(56) References Cited

U.S. PATENT DOCUMENTS

| | | | | |
|---|---|---|---|---|
| 5,365,455 | A | | 11/1994 | Tibetts et al. .................. 702/20 |
| 6,017,434 | A | * | 1/2000 | Simpson et al. ............. 204/466 |
| 6,208,941 | B1 | * | 3/2001 | Marks ......................... 382/129 |
| 6,236,944 | B1 | * | 5/2001 | Miller et al. ............. 435/287.1 |

OTHER PUBLICATIONS

Fluorescence Detection in Automated DNA Sequence Analysis, Lloyd M. Smith et al., *Nature*, Jun. 12, 1986, pp. 674–679.
Neural Networks for Automated Base–Calling of Gel–Based DNA Sequencing Ladders, C. Tibbetts et al. *Automated DNA Sequencing and Analysis*, Academic Press, San Fransico, 1994, pp. 219–230.(No month).
Cross–Talk Filtering in Four Dye Fluorescence–Based DNA Sequencing, Cristian Domnisoru Et al., *Electrophoresis* 2000, vol. 21, NO. 14, Aug. 2000, pp. 2983–2989.
Race is Over, Fredrick Golden, et al., *Time*, Jul. 3, 2000, pp. 19–23.
The Genome is Mapped. How What, Michael D. Lemonick, *Time*, Jul. 3, 2000, pp. 24–29.

* cited by examiner

*Primary Examiner*—Hal Wachsman
(74) *Attorney, Agent, or Firm*—MacMillan, Sobanski & Todd, LLC

(57) ABSTRACT

Raw DNA data is filtered with a multi-component analysis that is applied to the difference of the signal intensity on each of the raw DNA data signals to remove cross talk between the signals. The analysis is done before any baseline adjustment of the raw DNA data. Instead, the baseline adjustment occurs after the raw DNA data has been filtered. Additionally, an additional processing step is applied to the data to account for the non-linear nature of cross talk filtering. The additional processing step involves combining the signal with its derivative to account for the correlation of each of the data signals with the other three data signals.

19 Claims, 8 Drawing Sheets

METHOD FOR REDUCING CROSS-TALK WITHIN DNA DATA

BACKGROUND OF THE INVENTION

This invention relates in general to DNA data processing and in particular to an algorithm for reducing cross-talk between DNA data streams.

The structural analysis of DNA has an increasingly important role in modern molecular biology and is needed to support many research programs, including searching for clues to certain diseases. Accordingly, extensive research into DNA structure is ongoing. One of the most complex programs is the Human Genome Project which has the goal of determining the content of human DNA.

DNA is a nucleic acid consisting of chains of nucleotide monomers, or oligomers, that occurs in a specific sequence. The structural analysis of DNA involves determining the sequence of the oligomers. Currently, DNA sequencing begins with the separation of a DNA segment into DNA fragments comprising a stochastic array of the oligomers. The separation involves electrophoresis in DNA sequencing gels, such as denaturing polyacrylamide gels. One of two methods is typically used for the electrophoresis, either a chemical method is used that randomly cleaves the DNA segment or dideoxy terminators are used to halt the biosynthesis process of replication.

Each of the oligomers in the resulting stociastic array terminates in one of four identifying nitrogenous bases that are typically referred to by a letter. The bases are: adenine (A), cytosine (C), guanine (G) and thymine (T). Thus, the sequencing of the DNA can be accomplished by identifying the order of the bases A, C, G and T. This process is often referred as "base calling". However, DNA is extremely complex. For example, there are 3.1 billion biochemical letters in human DNA that spell out some 50,000 genes, automated base calling is highly desirable.

One method of automated base calling involves fluorescence detection of the DNA fragments. A schematic drawing of an apparatus for fluorescence detection is shown generally at 10 in FIG. 1. The apparatus 10 includes an upper buffer reservoir 12 connected to a lower buffer reservoir 14 by a gel tube 16. The gel tube 16 is formed from glass or quartz and has an inside diameter within the range of one to two mm. A detector 18 is mounted near the bottom of the tube 16. The detector 18 monitors the gel passing through the tube 16 and transmits the data to a computer 20.

The chemical method described above is used to separate a DNA segment into its base oligomers. A different colored fluorophore dye is used for each of the chemical reactions for the bases A, C, G and T. One of the fluorophore dyes attaches to each of the oligomers as a marker. The reaction mixtures are recombined in the upper reservoir 12 and co-electrophoresed down the gel tube 16. As the fluorophore dye labeled DNA fragments pass by the detector 18, they are excited by an argon ion laser that causes the dye to fluoresce. The dye emits a spectrum of light energy that falls within a range of wavelengths. A photo-multiplier tube in the detector 18 scans the gel and records data for the spectrum for each of the dyes. The resulting fluorescent bands of DNA are separated into one of four channels, each of which corresponds to one of the bases. The real time detection of the bases in their associated channels is transferred to the computer 20 which assembles the data into the sequence of the DNA fragment.

FIG. 2 illustrates an ideal data stream generated by the apparatus 10. As shown in FIG. 2, a color is associated with each of the four bases; with green identifying A; blue, C; black, G; and red, T. The data in each of the channels is shown as a horizontal line with the detection of a base appearing in real time as a pulse. The resulting time sequence of pulses received, and hence the DNA sequence, is shown as the top line in FIG. 2. However, the actual data stream differs from the ideal data stream because of several factors. First of all, the emission spectra of the different dyes overlap substantially. Because of the overlap, peaks corresponding to the presence of a single fluorophore dye can be detected in more than one channel. Additionally, the different dye molecules impart non-identical electrophoretic mobilities to the DNA fragments. Furthermore, as the photo-multiplier tube in the detector 18 scans the gel, data detection does not occur at the same time for the four signals. Finally, imperfections of the chemical separation method can result in substantial variations in the intensity of bands in a given reaction. Thus, a set of typical actual raw data streams is shown in FIG. 3. The notations along the vertical axis in FIG. 3 refer to wavelengths for the detected colors. As in FIG. 2, four data streams are shown with each data stream corresponding to one of the base identifiers, as indicated by the letters in parenthesis.

As illustrated by the flow chart shown in FIG. 4, it is known to enhance the raw data streams by a series of operations following the sampling of the DNA data in functional block 32. First, in functional block 34, high frequency noise is removed with a low-pass Fourier filter. Typically, each of the four data streams has a different base line level that varies slowly over time. These variations are corrected by passing the data through a high-pass Fourier filter in functional block 35.

The data streams are corrected with respect to signal strength, or magnitude, in functional block 36. This process is referred to a baseline adjustment. The data signal in each of the four channels is divided into a number of windows with each of the windows including approximately 30 signal peaks. The minimum signal strength is determined within each of the windows. A succession of segments is constructed connecting the consecutive minimum signal strengths. The absolute minima is determined for the consecutive segments. The minimum in each segment is then set to zero and the non-minimum points in the segment is adjusted by subtracting the difference between the absolute minimum and the minimum value for the segment. This signal strength adjustment is commonly referred to as baseline adjustment.

Next, a multicomponent analysis, or data filtering, is performed on each set of four data points, as shown in functional block 38. The filtering determines the amount of each of the four dyes present in the detector as a function of time. After filtering, the mobility shift introduced by the dyes is corrected in functional block 40 with empirically determined correction factors. Following this, the peaks present in the data are located in functional block 42. The application of the above series of operations to the raw data streams shown in FIG. 3 results in processed data streams in functional block 44 where the DNA sequence is read. The processed data streams are shown in FIG. 5. The corresponding DNA sequence is shown below the processed data streams in FIG. 5 and consists of the sequential combination of the four processed data streams A, T, G and C.

For the data processing described above, it is assumed that the transformation from raw data to filtered data is linear in order to develop the filter for removing the cross-talk. Assuming a linear transformation, the filtering step, shown in functional block 38 in FIG. 4, utilizes a transformation matrix, M, and involves a multi-component analysis that is embodied in the matrix M. With a multi-component analysis, the relationship between the measured signal $s_j$ and the actual fluorescence intensities $f_j$, with j=1, 2, 3 and 4, is given by the relationship:

$$s_j = \sum_{\substack{j=1 \\ i=1}}^{4} m_{i,j} \cdot f_j,$$

where $m_{i,j}$ is a constant coefficient indicating the cross talk between intensity signals i and j. Writing the above relationship in matrix form results in:

$$\underline{s} = M \cdot \underline{f}$$

where $\underline{s}$ and $\underline{f}$ are vectors with four elements and M is a 4×4 matrix.

Typically, the transformation matrix M is determined by a conventional method that includes an iterative process in which known raw data streams are processed through the matrix M and the matrix coefficients adjusted to provide the best signal separation possible for the data streams. The adjustment of the coefficients of the transformation matrix M is necessary because the data transformation is actually non-linear in nature.

To determine the actual intensities of the fluorescence, the matrix M is used to deconvolute the measured signals $\underline{s}$ into the actual fluorescence $\underline{f}$ by the following relationship:

$$\underline{f} = M^{-1} \cdot \underline{s}$$

In addition to the non-linearity of the data transformation, use of the transformation matrix M requires that the baseline adjustment of the data be applied to the data streams before filtering the data. The baseline adjustment is necessary because, as described above, the baseline within each fluorescent signal collected at the four different wavelengths typically varies with time. Also, each signal can have a different signal level. The algorithm typically used for the baseline adjustment first divides the entire data sequence in each channel into a number of windows. The baseline adjustment algorithm then finds a minimum value within each of the windows and constructs a line connecting the minimum values for each channel. Finally, the line connecting the minimum values is subtracted from the raw data at each data point in each channel. Unfortunately, the baseline adjustment can result in loss of information contained in the raw data and distort the signals. To regain the original data, additional steps, such as a Fourier-based filter for adjusting the base line or even a baseline cutoff is required. This adds complexity to the data processing. Accordingly, it would be desirable to both compensate for non-linear nature of the cross-talk filtering process and to eliminate the baseline adjustment of the raw data.

SUMMARY OF THE INVENTION

This invention relates to an algorithm for reducing cross-talk between DNA data streams.

The present invention is directed toward a multi-component analysis that is applied to the difference of the signal intensity on each of the four channels. This is done before any baseline adjustment of the raw data. Instead, baseline adjustment occurs after the raw data has been filtered. The present invention also adds an additional processing step to account for the non-linear nature of the cross talk filtering. The additional processing step includes combining the signals with their derivatives and accounts for the correlation of each of the data signals with the other three data signals.

The present invention contemplates a method for enhancing DNA raw data that includes providing an apparatus for collecting DNA data from dye-labeled DNA fragments, the DNA data being divided between a plurality of channels. The DNA data is passed through a first filter to reduce any cross-talk between data contained in the channels. The data is then passed through a second filter to reduce any non-linearity remaining after the first filtering process has been applied.

The reduction of cross talk between the channels includes determining difference values for the signals in each channel by subtracting the magnitudes of the signals in each channel at two consecutive sampling instants. A first multi-component analysis is applied to the difference values to deconvolute the data contained in the signals. The first multi-component analysis includes multiplying the data by a constant coefficient transformation matrix M.

The second filtering process to reduce the non-linearity remaining after the first filtering process includes determining derivative values for the signals obtained from the cross talk reduction filter. A multi-component analysis is applied to the derivative values to remove non-linear effects remaining after the first filtering process and the resulting data is then reconstructed to obtain the signal intensity. Similar to the first filter, the second multi-component analysis includes multiplying the data by a constant coefficient matrix T.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT

The inventors have found that accurate adjustment of the data baseline is hindered due to the difficulty of separating three main sources of the baseline variation. One of the sources of variation is variation in background lighting during data collection. Another source is the compound effect of consecutive bases of the same type. A third source is the presence of cross talk between the channels. The inventors believe that applying the baseline adjustment before the filtering of the signals can significantly distort the data.

Figure 1:
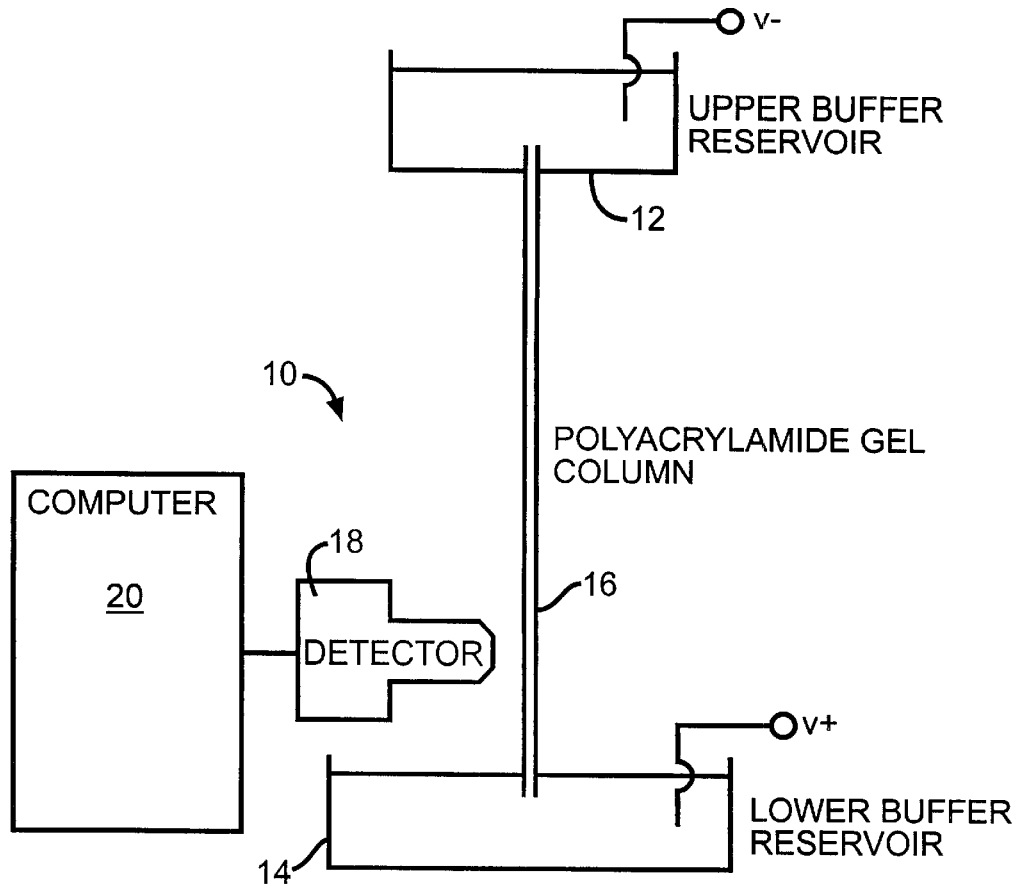
FIG. 1 is a schematic diagram of an automated DNA sequencer for detecting DNA sequences.
Figure 2:
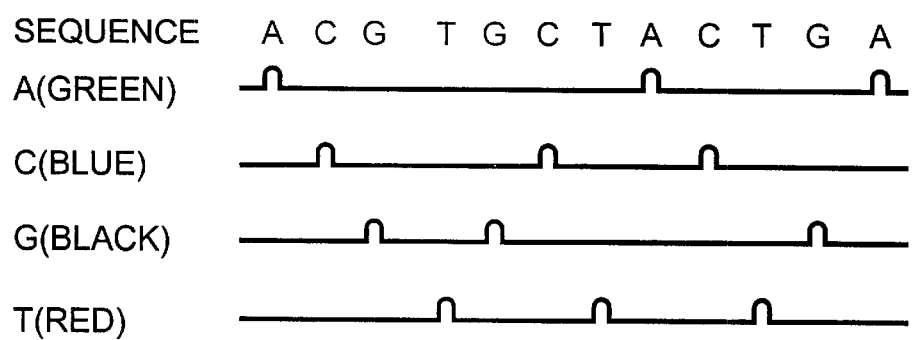
FIG. 2 is an idealized set of data streams obtained from the DNA sequencer shown in FIG. 1.
Figure 3:
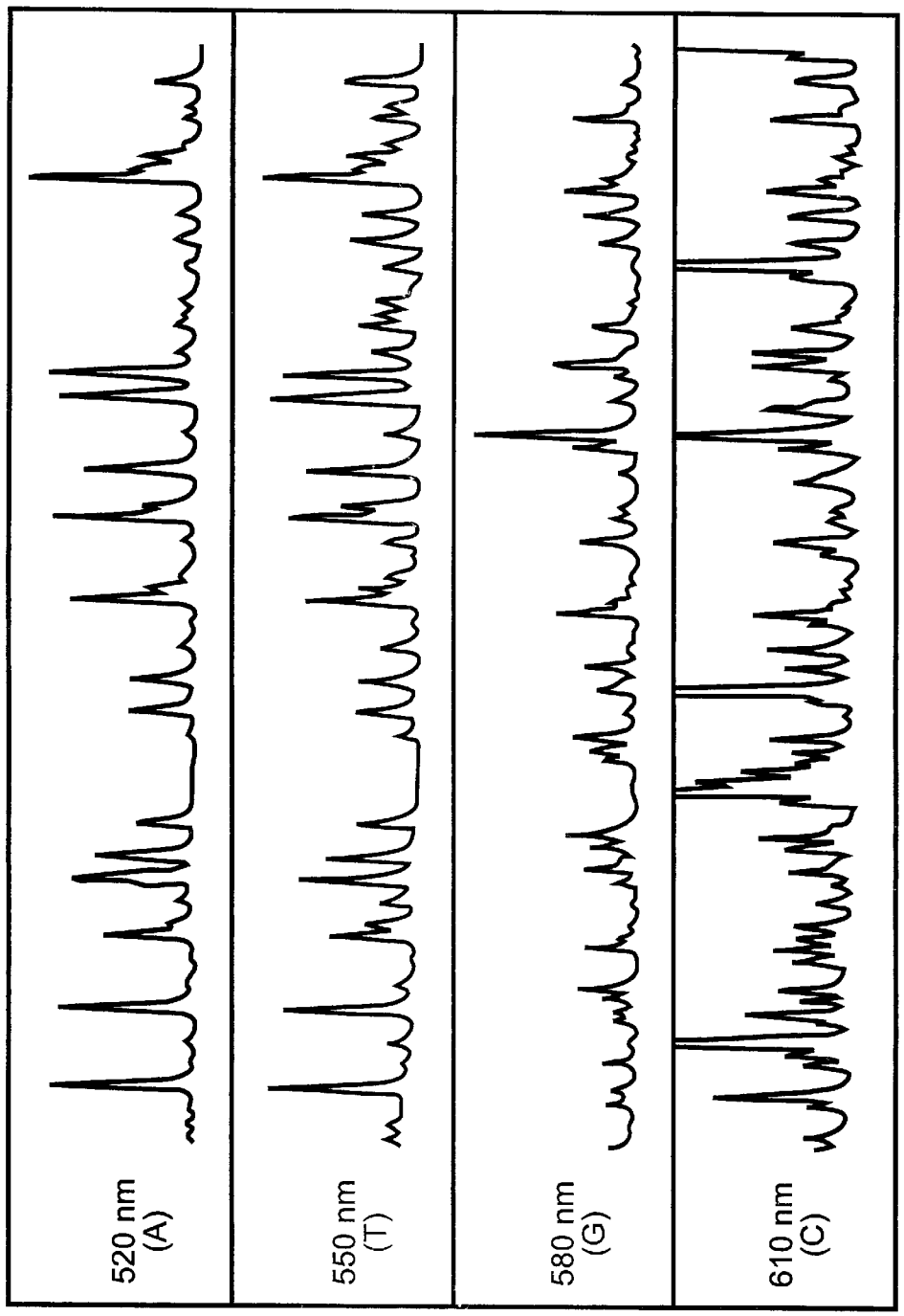
FIG. 3 shows a set of actual raw data streams obtained from the DNA sequencer shown in FIG. 1.
Figure 4:
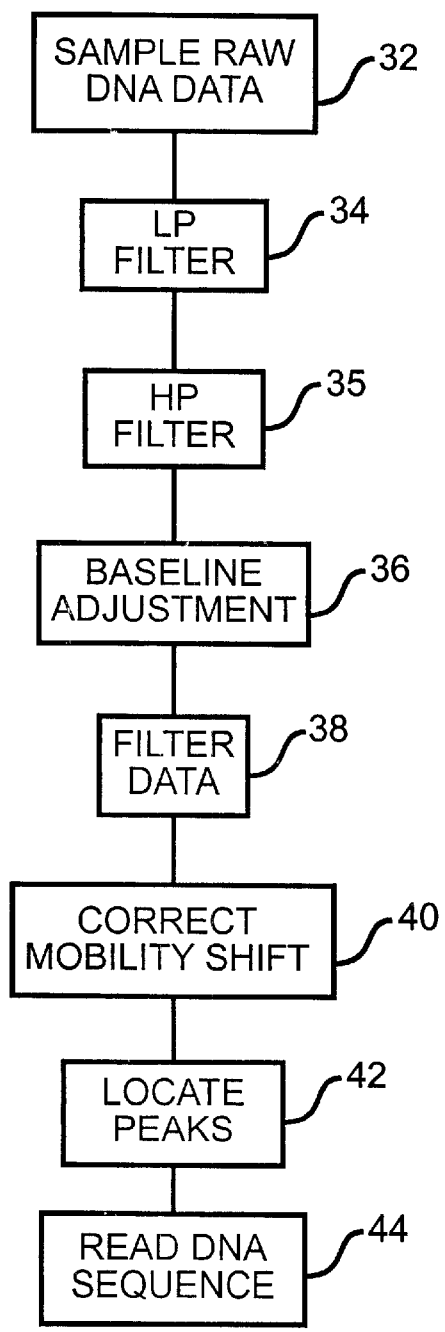
FIG. 4 is a flow chart for a prior art method for enhancing the raw DNA data streams shown in FIG. 3.
Figure 5:
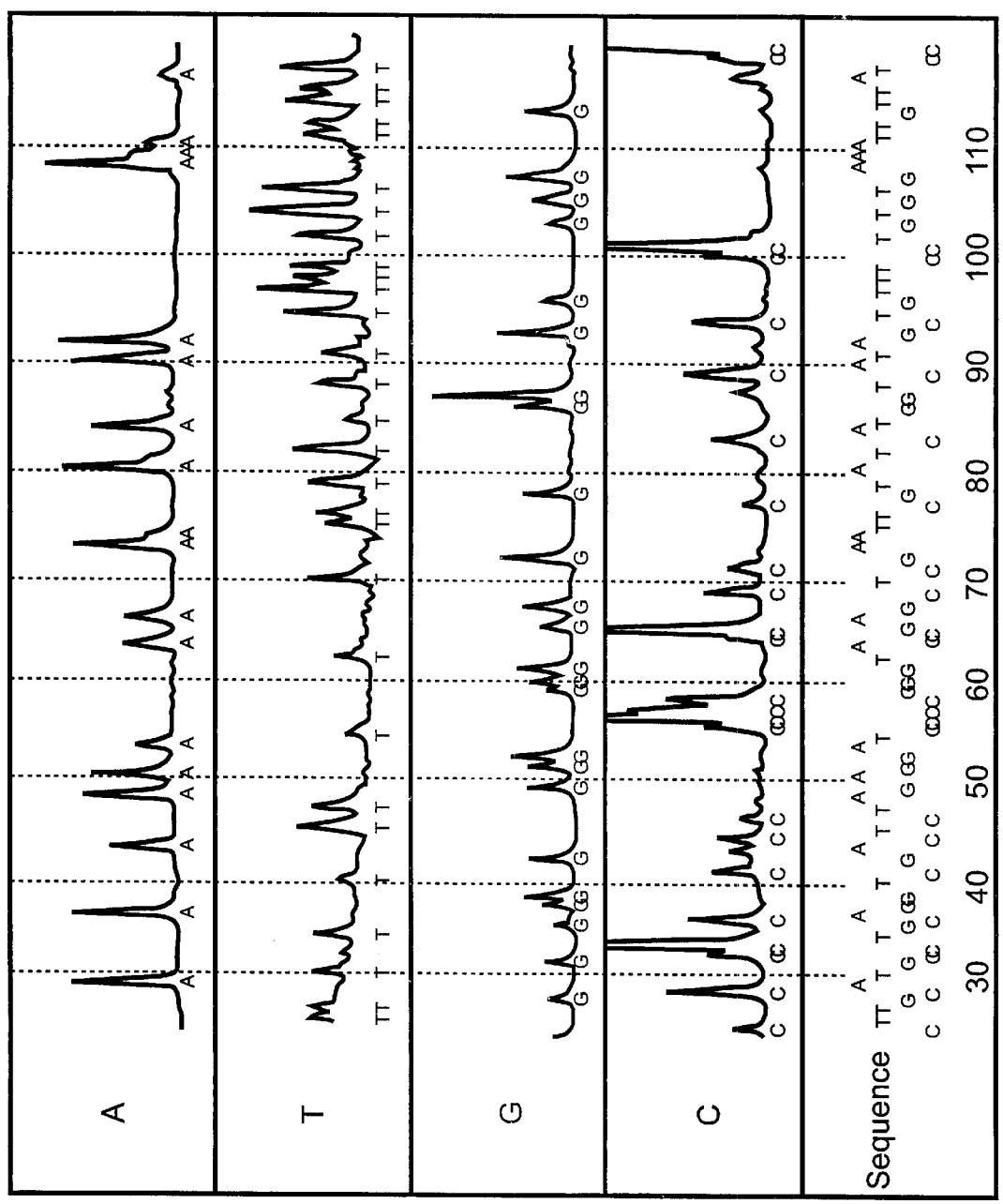
FIG. 5 shows the data from FIG. 3 after application of the prior art data enhancement method illustrated in FIG. 4.
Figure 6:
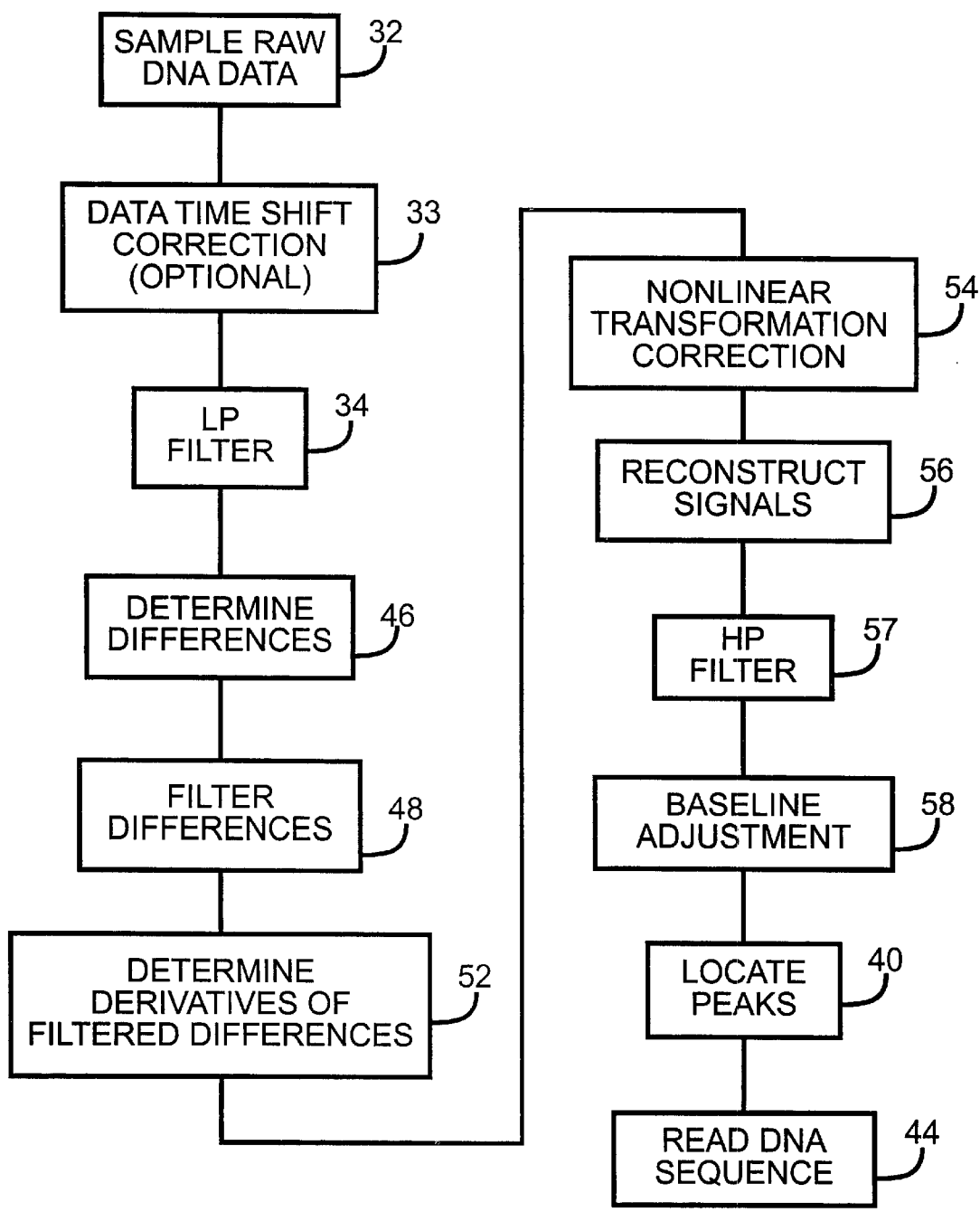
FIG. 6 is a flow chart for a method to enhance raw DNA data streams in accordance with the invention.

The present invention is directed toward an improved method for enhancing the raw DNA data streams to more accurately separate the streams. The method is illustrated by the flow chart shown in FIG. 6. Functional blocks shown in FIG. 6 that are the same as functional blocks shown in FIG. 4 have the same numerical designators. Thus, in functional block 32 raw DNA data streams are obtained by monitoring the passage of dye-labeled DNA fragments through the apparatus shown in FIG. 1. As described above, the raw data is separated into four channels and varies as a function of time. Because the four signals are not recorded at the same time, the information contained on one channel does not correspond to the information contained in the other three channels. Accordingly, the data stream in one of the four channels is selected as a time reference and the other three data streams are shifted in time in functional block 33 according to the position of the gel in the gel tube 16 when the raw data was read in the preceding functional block 32. As indicated in FIG. 6 this step is optional and is applied for certain test apparatus. For example, the step would be included for data obtained with ABI 373 and 377, but could be omitted for data obtained with ABI 3700. The data is then passed through a low pass Fourier filter in functional block 34 to remove high frequency noise.

The data points for any sample i at a corresponding point in time can be represented by $g_i$, $c_i$, $t_i$, and $a_i$. In functional block 46, the difference in the data points between two samples, i and i+1, at two consecutive sample times is determined by the relationships:

$$\Delta g_i = g_i + 1 - g_i;$$

$$\Delta c_i = c_i + 1 - c_i;$$

$$\Delta t_i = t_i + 1 - t_i; \text{ and}$$

$$\Delta a_i = a_i + 1 - a_i.$$

The data point differences, or signal variations, are filtered in functional block 48 by applying the transformation matrix M developed for cross-talk removal to obtain signal variation vectors $\underline{\Delta g}_i$, $\underline{\Delta c}_i$, $\underline{\Delta t}_i$, $\underline{\Delta a}_i$, that represent transformed data point differences as follows:

$$[\underline{\Delta g}_i, \underline{\Delta c}_i, \underline{\Delta t}_i, \underline{\Delta a}_i]T = M^{-1} \cdot [\Delta g_i, \Delta c_i, \Delta t_i, \Delta a_i]T$$

In the preferred embodiment, a second filtering step is then applied to the data in functional blocks 52 through 56. The second filtering step is based upon the inventor's observation that the transformation of the data from "detector space", or raw data, to "filtered space" is nonlinear in nature. The second filtering is described by the following operation:

$$\underline{\Delta s}_i = \underline{\Delta s}_i + \sum_{\substack{j=1 \\ j \neq i}}^{4} t_{i,j} \cdot \underline{\Delta s}'_j;$$

Where $\underline{\Delta s}_i$ is the data signal variation and is given by:

$$\underline{\Delta s}_i = \begin{vmatrix} \underline{\Delta g}_i \\ \underline{\Delta c}_i \\ \underline{\Delta t}_i \\ \underline{\Delta a}_i \end{vmatrix}$$

and $\underline{\Delta s}_j'$ is the derivative of the data signal variation and is given by:

$$\underline{\Delta s}'_j = \begin{vmatrix} \underline{\Delta g}'_j \\ \underline{\Delta c}'_j \\ \underline{\Delta t}'_j \\ \underline{\Delta a}'_j \end{vmatrix}$$

The above formula can be written in matrix form as:

$$\underline{\Delta s} = \underline{\Delta s} + T \cdot \underline{\Delta s}';$$

where:

$$\underline{\Delta s} = \begin{vmatrix} \underline{\Delta g} \\ \underline{\Delta c} \\ \underline{\Delta t} \\ \underline{\Delta a} \end{vmatrix}$$

The matrix T is a constant coefficient 4×4 transformation matrix that accounts for the correlation of each of the signals with the other three. The transformation matrix T is determined by the same conventional method that is used to determine the cross talk removal matrix M, except that different known data streams are used. Thus, the determination of T includes an iterative process in which known data streams are processed through the matrix T and the matrix coefficients adjusted to provide the desired output data. Accordingly, in functional block 52, derivatives $\underline{\Delta s}'$ of the signal variation $\underline{\Delta s}$ are calculated. The signal derivatives are filtered by application of the matrix T in functional block 54 in accordance with the relationships shown above. The result of the second filtering operation is signals, $\underline{\Delta g}$, $\underline{\Delta c}$, $\underline{\Delta t}$ and $\underline{a}$.

The signals $\underline{\Delta g}$, $\underline{\Delta c}$, $\underline{\Delta t}$ and $\underline{\Delta a}$ are used in functional block 56 to reconstruct the signals of the four fluorophores with the following operation:

$$\underline{s}_i + 1 = \underline{\Delta s}_i + \underline{s}_i;$$

Up to a constant value, the vectors $\underline{g}_i$, $\underline{c}_i$, $\underline{t}_i$ and $\underline{a}_i$ included in $\underline{s}_i$ contain recomposted signals with the cross-talk removed and non-linearity corrected. However, the signals are still shifted relative to each other and with respect to a baseline due to variations in the electrophoresis process caused by such things as temperature changes, variation in applied voltages, gel variations and the like. Accordingly, the signals are passed though a high-pass Fourier filter in functional block 57. Thus, the present invention contemplates separating the high-pass filtering operation from the low-pass filtering operation illustrated in FIG. 4.

The data streams are corrected with respect to signal strength, or magnitude, in functional block 58. This process is referred to a baseline adjustment. The data signal in each of the four channels is divided into a number of windows, which, in the preferred embodiment will contain approximately 30 peaks each. The minimum signal strength is determined within each of the windows. A succession of segments is constructed connecting the consecutive minimum signal strengths. The absolute minima is determined for the consecutive segments. The minimum in each segment is then set to zero and the non-minimum points in the segment is adjusted by subtracting the difference between the absolute minimum and the minimum value for the segment.

As previously described, the peaks of the signals are located in functional block 40 and the DNA sequence read in functional block 44.

EXAMPLE

Figure 7:
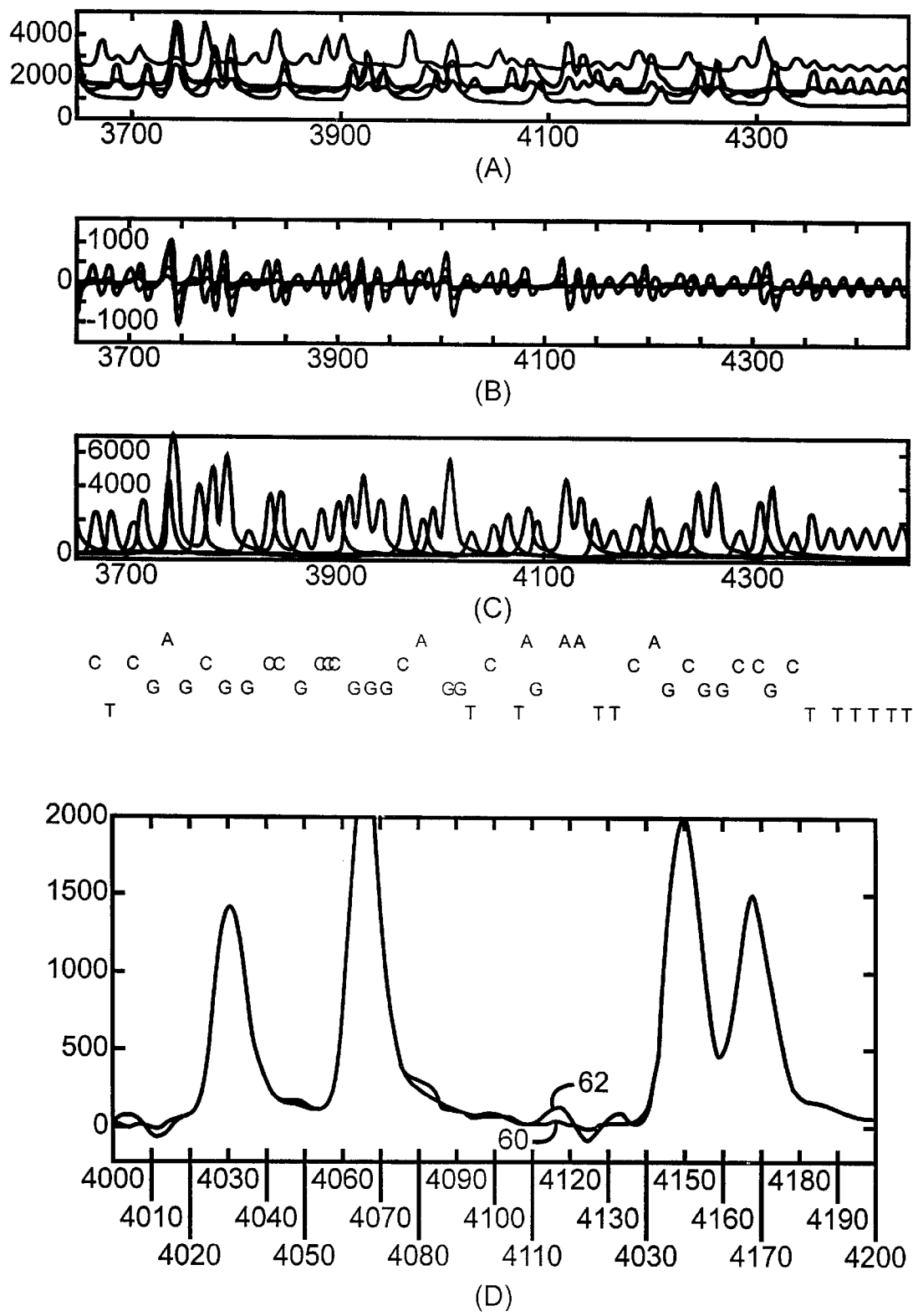
FIG. 7 illustrates the enhancement of DNA raw data streams as a result of the method shown in FIG. 6.

Referring again to the drawings, there is illustrated in FIG. 7, an example of the method for enhancing DNA data shown in FIG. 6 and described above. Part A of FIG. 7 shows a section of a raw DNA data sequence. As described above, the first step in the method involves determining the differences, or changes, in the signal amplitudes. Accordingly, Part B of FIG. 7 illustrates the variation of the four signals after the amplitude shift in functional block 46 of FIG. 6 has been completed. The signals shown in Part B of FIG. 7 are then operated upon the matrix M, which, for this example, is given by:

$$M = \begin{vmatrix} 1 & 0 & 0.47 & 0.19 \\ 0.15 & 1 & 0.05 & 0.36 \\ 0.07 & 0 & 1 & 0 \\ 0.36 & 0.14 & 0.22 & 1 \end{vmatrix}$$

The nonlinear transformation correction is applied by operating upon the signals with the matrix T, which, for this example, is given by:

$$T = \begin{vmatrix} 0 & 0 & 0.1 & -0.15 \\ -0.06 & 0 & -0.01 & -0.05 \\ 0.05 & 0 & 0 & 0 \\ 0.13 & 0.05 & 0.08 & 0 \end{vmatrix}$$

The result of the second filtering step is shown in Part C of FIG. 7. A portion of the curve show in Part C of FIG. 7 is enlarged and labeled 60 in Part D of FIG. 7. Also shown in FIG. Part D of FIG. 7 is a portion of a corresponding curve 62 that would result without the second filtering step to eliminate the non-linarities. Part D of FIG. 7 demonstrates that the noise in the baseline is clearly attenuated by the second filtering step. The overall result can be compared to that obtained with a highly adaptive filter. The final DNA sequence is shown below Part C of FIG. 7.

Similar experiments carried out by the inventors have shown that by performing the baseline adjustment after filtering out the cross talk between the channels, the data content of the signals is better preserved. The inventors believe that the most important feature of their method is the use of the variation of the signal rather than the actual value for removal of the cross talk. By using the variation of the signal, it is possible to reverse the order in which the cross talk removal and baseline adjustment are performed. To further filter the signals, the inventors have extended their method to account for the nonlinear dependency between the raw data and the actual signals. The method illustrated and described above helps preserve the information contained in the raw DNA data.

Figure 8:
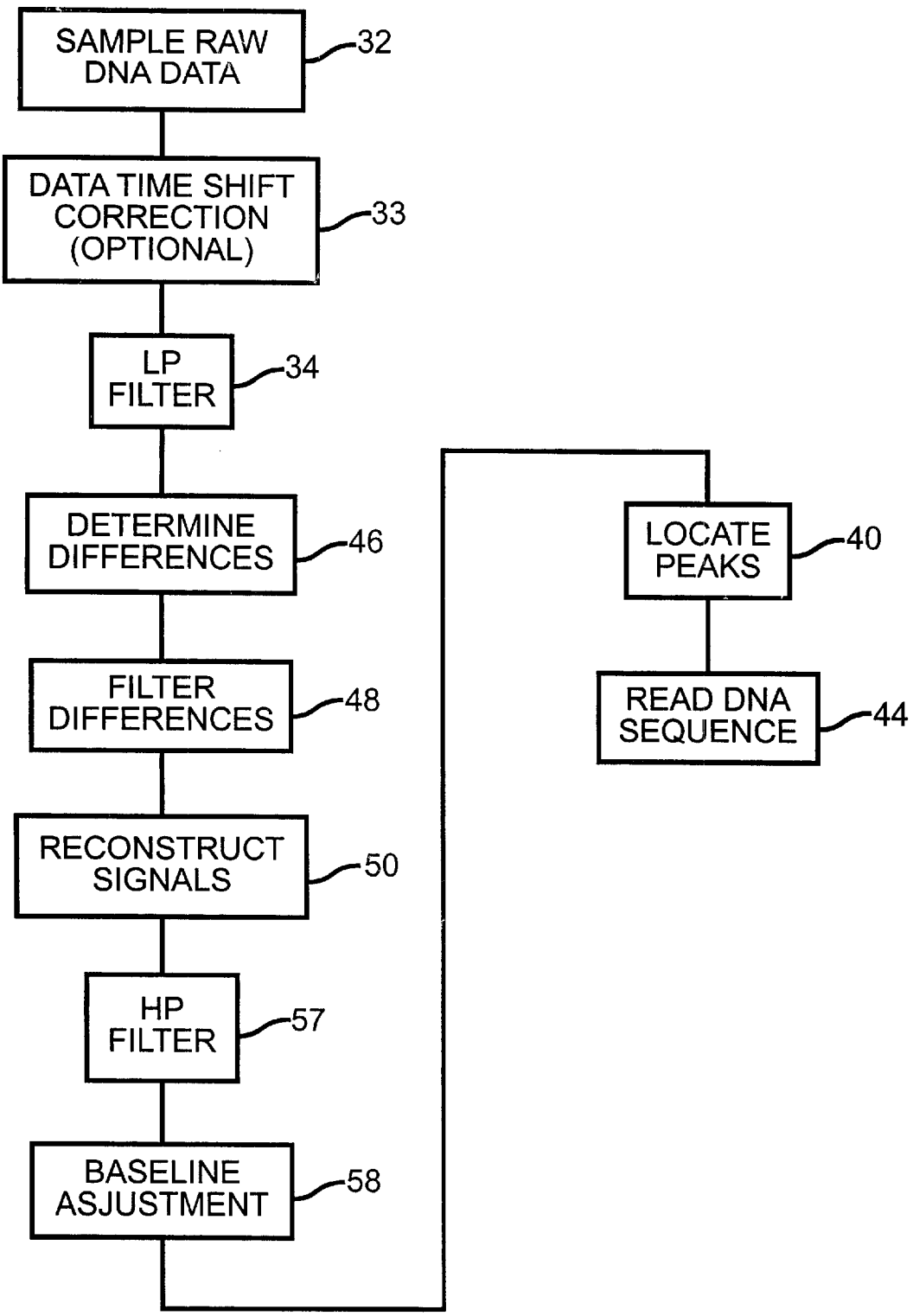
FIG. 8 is a flow chart for an alternate embodiment of the method shown in FIG. 6.

While the preferred embodiment has been illustrated and described above, it is also possible to practice the invention with an alternate embodiment of the method as shown in FIG. 8. The functional blocks in FIG. 8 that are the same as the functional blocks shown in FIGS. 4 and 6 have the same numerical identifiers. In the flow chart shown in FIG. 8, the cross talk filtering step shown in functional block 38 in FIG. 4 has been replaced with the use of the variation of the signal rather than the actual value for removal of the cross talk, as shown in functional blocks 46 and 48 in FIG. 6. Additionally, the high pass filtering, as shown in functional block 57, and the base line adjustment, as shown in functional block 58 occur after the filtering of the cross talk. Therefore, the method shown in FIG. 8 would produce the data shown in Part D of FIG. 7 and is equivalent to the preferred embodiment with the second filtering operation removed. While the method shown in FIG. 8 will not provide the degree of enhancement obtained with the method shown in FIG. 6, the inventors believe that the method shown in FIG. 8 will provide a degree of enhancement that is better than that obtained with the prior art method shown in FIG. 4.

Figure 9:
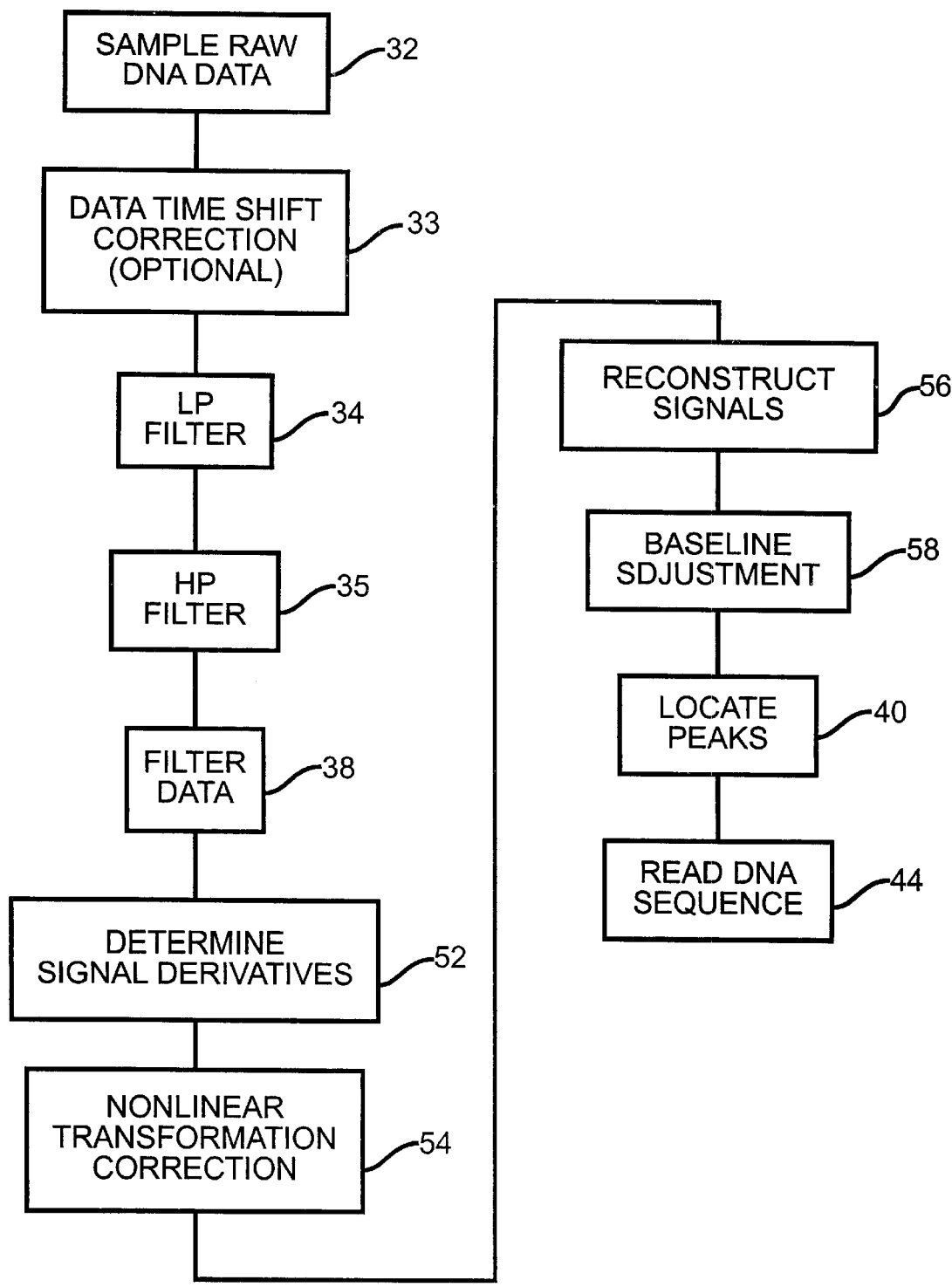
FIG. 9 is a flow chart for another alternate embodiment of the method shown in FIG. 6.

Similarly, the inventors contemplate a second alternate embodiment of their invention, as illustrated in FIG. 9. The functional blocks in FIG. 9 that are the same as the functional blocks shown in FIGS. 4 and 6 have the same numerical identifiers. The flow chart in FIG. 9 is similar to the prior art method shown in FIG. 4, except that the optional data time shift correction in functional block 33 and the second filtering step in functional blocks 52 and 54 have been added. Also, the baseline adjustment shown in functional block 58 occurs after signals are reconstructed in functional block 56. While the method shown in FIG. 9 will not provide the degree of enhancement obtained with the method shown in FIG. 6, the inventors believe that the method shown in FIG. 9 will provide a degree of enhancement that is better than that obtained with the prior art method shown in FIG. 4.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A method for enhancing DeoxyriboNucleic Acid (DNA) raw data comprising the steps of:

(a) providing an apparatus for collecting DNA data from dye-labeled DNA fragments, the DNA data being divided between a plurality of channels;

(b) passing the DNA data contained in each of the plurality of channels through a filter to reduce crosstalk between DNA data contained in each of the channels; and (c) adjusting the baseline of the DNA data contained in each of the channels.

2. The method according to claim 1 wherein the reduction of cross talk between each of the channels in step (b) includes the steps of:

(b1) determining difference values for the signals in each channel that correspond to the DNA data by subtracting the magnitudes of the signals in each of the channels at two consecutive sampling instants;

(b2) applying a multi-component analysis to the difference values obtained in step (b1) to deconvolute the DNA data contained in the signals; and (b3) recombining the deconvoluted difference data with the corresponding signals at the specific sampling instant to obtain the signal intensity.

3. The method according to claim 2 wherein the multi-component analysis in step (b2) includes multiplying the signals corresponding to the DNA data by a constant coefficient transformation matrix M.

4. The method according to claim 3 wherein the multi-component analysis in step (b2) includes the following operation:

$$\Delta \underline{s}_j = \sum_{\substack{j=1 \\ i=1}}^{4} m_{i,j} \cdot \Delta s_j ;$$

where $\Delta s_j$ represents the variation of the measured signal $s_j$ in each channel that corresponds to the DNA data between two consecutive signal measurements and $\Delta \underline{s}_j$ represents filtered signal variation with crosstalk removed; and $m_{i,j}$ is a constant coefficient indicating the cross talk between measured signal varation $s_j$ and the filtered signal variation $\Delta \underline{s}_j$.

5. The method according to claim 4 wherein, prior to step (b), the signal corresponding to the DNA data is passed through a low pass filter.

6. The method according to claim 5 further including, before adjusting the baseline of the DNA data in step (c), passing the signal corresponding to the DNA data in each of the channels through a high pass filter.

7. The method according to claim 6 further including, subsequent to the baseline adjustment in step (c), locating peak values in each channel and reading a DNA sequence from a combination of the DNA data contained in each of the channels.

8. A method for enhancing DeoxyriboNucleic Acid (DNA) raw data comprising the steps of:

(a) providing an apparatus for collecting DNA data from dye-labeled DNA fragments, said data divided between a plurality of channels;

(b) passing the DNA data in each channel through a first filter to reduce cross-talk between DNA data contained in each of the channels;

(c) passing the filtered DNA data in each channel from step (b) through a second filter to reduce any non-linearity remaining after the first filtering process in step (b);

(d) recombining the filtered DNA data in each channel from step (c) with corresponding signals at a specific sampling instant to obtain a filtered signal intensity for each channel; and (e) adjusting the baseline of the DNA data contained in each of the channels.

9. The method according to claim 8 wherein the second filtering process in step (c) includes the steps of:

(c1) determining derivative values for the filtered DNA data obtained from the first filter in step (b); and (c2) applying a multi-component analysis to the derivative values obtained in step (c1) to remove non-linear effects remaining after the first filtering process.

10. The method according to claim 9 wherein the multi-component analysis in step (c2) includes multiplying the derivative values obtained in step (c1) by a constant coefficient transformation matrix T.

11. The method according to claim 10 wherein the multi-component analysis in step (c2) includes the following operation:

$$\Delta \underline{s}_i = \Delta s_i + \sum_{\substack{j=1 \\ j \neq i}}^{4} t_{i,j} \cdot \Delta s'_j ;$$

where $\Delta \underline{s}_i$ represents the variation of the DNA data after the second filtering process in step (c);

$\Delta s_i$ represents the variation of the DNA data after the first filtering process in step (b);

$\Delta s_i'$ represents the time derivative of $\Delta s_i$; and $t_{i,j}$ is a constant coefficient indicating an approximated linear relationship between intensity $\Delta s_i$ and $\Delta s_i'$.

12. The method according to claim 11 wherein the reduction of cross talk between each of the channels in step (b) includes the steps of:

(b1) determining difference values for the DNA data in each channel by subtracting the magnitudes of the DNA data in each channel at two consecutive sampling instants; and (b2) applying a multi-component analysis to the difference values obtained in step (b1) to deconvolute the DNA data contained in each channel.

13. The method according to claim 12 wherein the multi-component analysis in step (b2) includes multiplying the DNA data by a constant coefficient transformation matrix M.

14. The method according to claim 13 wherein the multi-component analysis in step (b2) includes the following operation:

$$\Delta \underline{s}_j = \sum_{\substack{j=1 \\ i=1}}^{4} m_{i,j} \cdot \Delta s_j ;$$

where $\Delta s_j$ represents the variation of the measured DNA data $s_j$ between two consecutive DNA data measurements and $\Delta \underline{s}_j$ represents filtered DNA data variation with crosstalk removed; and $m_{i,j}$ is a constant coefficient indicating the cross talk between measured DNA data varation $s_j$ and the filtered signal variation $\Delta \underline{s}_j$.

15. The method according to claim 14 wherein, prior to step (b), the DNA data is passed through a low pass filter.

16. The method according to claim 15 further including, before adjusting the baseline of the DNA data in step (e), passing the DNA data through a high pass filter.

17. The method according to claim 16 further including, subsequent to the baseline adjustment in step (e), locating peak values in the DNA data in each channel and reading a DNA sequence from a combination of the DNA data contained in each of the channels.

18. An algorithm for processing DeoxyriboNucleic Acid (DNA) data, the DNA data being divided between a plurality of channels, the algorithm comprising the steps of:

(a) measuring a signal in each channel that corresponds to the DNA data associated with the channel;

(b) determining difference values for the measured signals in each channel by subtracting the magnitudes of the measured signals in each channel at two consecutive sampling instants;

(c) passing the difference values for the measured signals in each of the channels through a first filter to reduce cross-talk between the measured signals contained in the channels that includes the following operation:

$$\underline{\Delta s}_j = \sum_{\substack{j=1 \\ i=1}}^{4} m_{i,j} \cdot \Delta s_j;$$

where $\Delta s_j$ represents the variation of the measured signal $s_j$ between two consecutive signal measurements and $\underline{\Delta s}_j$ represents filtered measured signal variation with crosstalk removed; and $m_{i,j}$ is a constant coefficient indicating the cross talk between measured signal varation $s_j$ and the filtered signal variation $\underline{\Delta s}_j$;

(d) passing the filtered measured signals from step (c) in each of the channels through a second filter to reduce any non-linearity remaining after the first filtering process in step (c) that includes the following operation:

$$\underline{\underline{\Delta s}}_i = \underline{\Delta s}_i + \sum_{\substack{j=1 \\ j \neq i}}^{4} t_{i,j} \cdot \underline{\Delta s}'_j;$$

where $\underline{\underline{\Delta s}}_i$ represents the variation of the data signal after the second filtering process;

$\underline{\Delta s}_i$ represents the variation of the measured signal after the first filtering process in step (c);

$\underline{\Delta s}_j'$ represents the time derivative of $\underline{\Delta s}_i$; and $t_{i,j}$ is a constant coefficient indicating the non-linear relationship between $\underline{\Delta s}_i$ and $\underline{\Delta s}_j'$;

(e) reconstructing the measured signals in each of the channels; and (f) adjusting the baseline of the measured signal contained in each of the channels.

19. An algorithm for processing DeoxyriboNucleic Acid (DNA) data, the DNA data being divided between a plurality of channels, the algorithm comprising the steps of:

(a) passing the DNA data in each channel through a first filter to reduce cross-talk between DNA data contained in each of the channels that includes the following operation:

$$s_j = \sum_{\substack{j=1 \\ i=1}}^{4} m_{i,j} \cdot f_j;$$

where $s_j$ represents a signal corresponding to the filtered DNA data and $f_j$ represents fluorescence intensity; and $m_{i,j}$ is a constant coefficient indicating the cross talk between intensity signals i and j;

(b) passing the filtered DNA data signal in each of the channels through a second filter to reduce any non-linearity introduced by the first filtering process in step (a) that includes the following operation:

$$\underline{s}_i = s_i + \sum_{\substack{j=1 \\ j \neq i}}^{4} t_{i,j} \cdot s'_j;$$

where $\underline{s}_i$ represents the variation of the DNA data signal after the second filtering process in step (b);

$s_i$ represents the measured signal after the first filtering process in step (a);

$\underline{s}_j'$ represents the time derivative of $\underline{s}_i$; and $t_{i,j}$ is a constant coefficient indicating the non-linear relationship between intensity $\underline{\Delta s}_i$ and $\underline{\Delta s}_j'$;

(c) reconstructing the DNA data signals in each of the channels; and (d) adjusting the baseline of the DNA data contained in each of the channels.

\* \* \* \* \*